United States Patent
Bonrath et al.

(10) Patent No.: US 9,045,404 B2
(45) Date of Patent: Jun. 2, 2015

(54) PROCESS FOR THE MANUFACTURE OF 2-PENTYN-1-OL

(75) Inventors: Werner Bonrath, Freiburg (DE); Francesco Pace, Stein (CH); Jocelyn Fischesser, Wittenheim (FR); Konrad Witzgall, Wehr (DE)

(73) Assignee: DSM IP ASSETS B.V., Heerlen (NL)

( * ) Notice: Subject to any disclaimer, the term of this patent is extended or adjusted under 35 U.S.C. 154(b) by 610 days.

(21) Appl. No.: 13/389,110

(22) PCT Filed: Aug. 5, 2010

(86) PCT No.: PCT/EP2010/061411
§ 371 (c)(1),
(2), (4) Date: Apr. 17, 2012

(87) PCT Pub. No.: WO2011/015623
PCT Pub. Date: Feb. 10, 2011

(65) Prior Publication Data
US 2012/0197046 A1    Aug. 2, 2012

(30) Foreign Application Priority Data
Aug. 6, 2009   (EP) .................................... 09167367

(51) Int. Cl.
C07C 29/36    (2006.01)
C07C 29/00    (2006.01)
C07C 41/48    (2006.01)
C07C 43/303   (2006.01)
C07C 41/54    (2006.01)
C07C 29/10    (2006.01)

(52) U.S. Cl.
CPC ................. *C07C 41/48* (2013.01); *C07C 29/10* (2013.01); *C07C 41/54* (2013.01)

(58) Field of Classification Search
USPC .................................................. 568/597, 873
See application file for complete search history.

(56) References Cited

FOREIGN PATENT DOCUMENTS

DE    32 45 047    6/1983
EP    1 238 944    9/2002

OTHER PUBLICATIONS

Whitaker et al., 2-Methoxypropene, e-EROS Encyclopedia of Reagents for Organic Synthesis, 2001, pp. 1-3.*
International Search Report for PCT/EP2010/061411, mailed Feb. 7, 2011.
Zakharkin et al., "Synthesis of some acetylenic alcohols", *Bulletin of the Academy of Sciences of the USSR*, Eng. Translation, Oct. 5, 1964, pp. 871-872.
Just et al., "Total synthesis of 11(R,S)-HETE (13)", *Tetrahedron Letters*, vol. 23, No. 13, Jan. 1, 1982, pp. 1331-1334.
Kotke, "Generally Applicable Organocatalytic Tetrahydropyranylation of Hydroxy Functionalities with Very Low Catalyst Loading", *Synthesis*, No. 5, Feb. 8, 2007, pp. 779-790.
Jiang et al., "Chiral Synthesis of Methyl (2R, 3S)-2-Methyl-3-Hydroxypentanoate", *Chemical Research and Application*, vol. 11, No. 5, 1999, pp. 521-522.
Brandsma, "Preparative Acetylenic Chemistry", *Studies in Organic Chemistry 34*, 1988, pp. 47-50.
Lampilas et al., "Convergent Stereospecific Total Synthesis of Monochiral Monocillin I Related Macrolides", *Tetrahedron Letters*, vol. 33, No. 6, 1992, pp. 773-776.

* cited by examiner

*Primary Examiner* — Rosalynd Keys
(74) *Attorney, Agent, or Firm* — Nixon & Vanderhye P.C.

(57) ABSTRACT

The present invention is directed to a process for the manufacture of 2-pentyn-1-ol starting from 2-propyn-1-ol via the following intermediates (I), (II) wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl, as well as to the intermediates themselves.

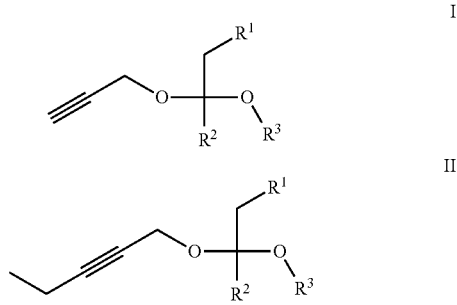

19 Claims, 1 Drawing Sheet

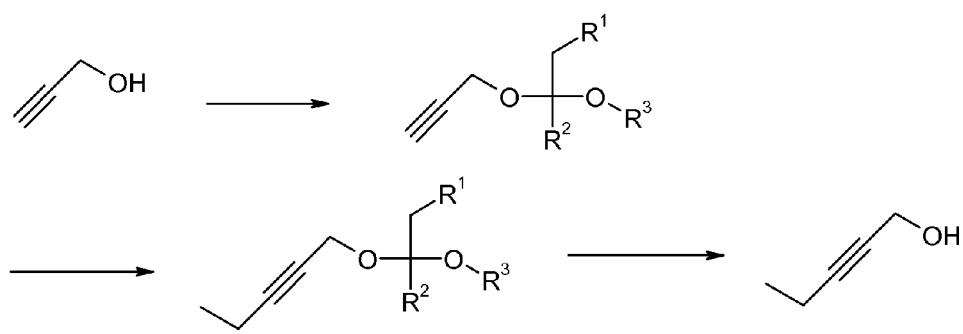

PROCESS FOR THE MANUFACTURE OF 2-PENTYN-1-OL

This application is the U.S. national phase of International Application No. PCT/EP2010/061411 filed 5 Aug. 2010 which designated the U.S. and claims priority to EP Patent Application No. 09167367.3 filed 6 Aug. 2009, the entire contents of each of which are hereby incorporated by reference.

2-Pentyn-1-ol is an attractive compound, because it is an intermediate for the flavor and fragrances industry, e.g. for jasmonate type flavors (see W. Y. Lee, S. Yang, Se Y. Jang, S. Y. Lee, *Bulletin of the Korean Chemical Society* 1991, 12, 26; T. Joshida, A. Yamaguchi, A. Kamatsu, *Agricult. Biol. Chem.* 1966, 30, 370).

An object of the present invention was to find a procedure which can be implemented in industrial scale.

In the literature several methods for the preparation of 2-pentyn-1-ol are already described. In the past methods starting from butyne and formaldehyde (gas) were well known. Butyne was e.g. treated with ethyl magnesium bromide to the corresponding butyne-magnesium compound followed by reaction with formaldehyde. After hydrolysis and distillation 2-pentynol could be isolated in approximately 60% yield (see Y. Tchai Lai, *Bull. Chim Soc. France* 1933, 53, 682; K.-E. Schulte, W. Engelhardt, *Archiv Ber. Dt. Pharm. Soc.* 1954, 287, 495; JP 50 049 213). Similar reactions are described for the lithium salts of butyne; see e.g. U.S. Pat. No. 4,143,230 where the reaction of 1-butynyl lithium with paraformaldehyde to 2-pentyn-1-ol is described.

A further object of the present invention is to avoid the use of formaldehyde, formalin or paraformaldehyde in the production of 2-pentyn-1-ol, since they are carcinogen, mutagen and reprotoxic.

Another method for the synthesis of 2-pentynol starts from chlorobutynol, which is treated with methyl magnesium halides in 57-65% yield (see J. Colonge, G. Descotes, *Bull Soc Chim. France* 1959, 815; A. A. Kraevskii, B. Yu. Pyatnova, G. I, Myagkova., I. K. Sarycheva, N. A. Preobrazhenskii, *Doklady Akademii Nauk SSSR* 1962, 146, 1349; A. A. Kraevskii, I. K. Sarycheva, N. A. Preobrazhenskii, *Zhurnal Obshchei Khimii* 1963, 33, 1831.). These methods have several disadvantages, like halide handling, low yield, large amount of waste.

Another route to 2-pentyn-1-ol was disclosed by Wu (see J. Wu, X. Kuang, Y. Tang, *Huaxue Yanjiu Yu Yingyong* (*Chemical Research and Application*) 1999, 11 (5), 521-522). Starting from propargyl alcohol and lithium amide addition followed by ethyl bromide addition 2-pentyn-1-ol was obtained.

In a different approach to the synthesis of 2-pentyn-1-ol the starting material propargyl alcohol was treated with dihydropyran to tetrahydro-2-(2-propynyloxy)-2H-pyran (compound A) in 86% yield, followed by sodium amide and ethyl bromide addition (see T. Joshida, A. Yamaguchi, A. Kamatsu, *Agricult. Biol. Chem.* 1966, 30, 370). The resulting 2-pentyne-1-yl-2-tetrahydropyranyl ether (2-(pent-2-ynyloxy)tetrahydro-2H-pyran=compound B) was extracted with ether and purified by distillation (96% yield). 2-Pentyn-1-ol was synthesized from this material by treatment with an aqueous 85% phosphorus acid at 145-155° C. in 82% yield, the overall yield starting from propargyl alcohol was 67.7%. A similar process is also described in U.S. Pat. No. 4,186,141.

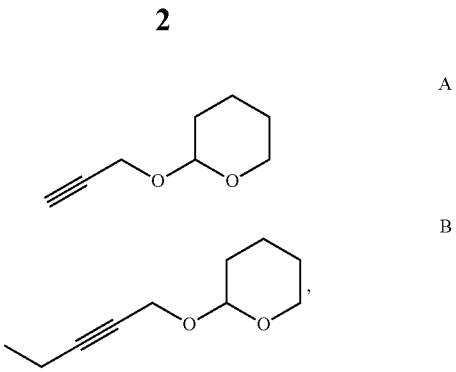

Main disadvantage is the difficult separation of the protecting group after work-up from the final product. This would be too expensive when working on industrial scale.

Thus, a further object of the present invention is to avoid the use of 2-(pent-2-ynyloxy)tetrahydro-2H-pyran as intermediate for 2-pentyn-1-ol.

These needs are fulfilled by the process of the present invention for the manufacture of 2-pentyn-1-ol starting from 2-propyn-1-ol which comprises the following steps:

a) preparing a ketal of the formula I starting from 2-propynol in the presence of an acid catalyst;

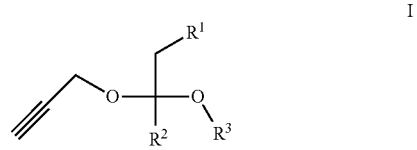

b) reacting the ketal of formula I with an alkyl halide selected from the group consisting of ethyl chloride, ethyl bromide and ethyl iodide to the ketal of formula II in the presence of ammonia and a lithium compound selected from the group consisting of lithium amide, alkyl lithium and aryl lithium;

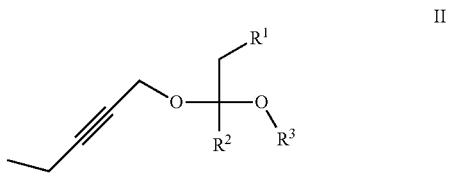

c) reacting the ketal of the formula II to 2-pentyn-1-ol in the presence of an acid catalyst and a protic solvent;

wherein $R^1$ is H or linear $C_{1-6}$ alkyl, $R^2$ is linear $C_{1-6}$ alkyl or branched $C_{3-6}$ alkyl, and $R^3$ is linear $C_{1-6}$ alkyl.

This process is shown in FIG. 1.

The expression "linear $C_{1-6}$ alkyl" encompasses methyl, ethyl, n-propyl, n-butyl, n-pentyl and n-hexyl. The term "branched $C_{3-6}$ alkyl" encompasses iso-propyl, iso-butyl, tert-butyl, 2-pentyl, 3-pentyl, 2-methylbutyl, 3-methylbutyl, 3-methyl-2-butyl, 2,2-dimethyl-propyl, 2-hexyl, 3-hexyl, 3-methyl-2-pentyl, 3-methyl-3-pentyl, 2,2-dimethyl-butyl, 3,3-dimethyl-butyl, 2,3-dimethyl-2-butyl, 2,3-dimethyl-3-butyl and 3,3-dimethyl-2-butyl.

Preferred compounds of formula I and II are those, wherein $R^1$ is H or linear $C_{1-3}$ alkyl, and/or $R^2$ is linear $C_{1-3}$ alkyl and/or $R^3$ is linear $C_{1-3}$ alkyl; more preferred are those, wherein $R^1$ is H or linear $C_{1-3}$ alkyl, and $R^2$ and $R^3$ are independently from each other linear $C_{1-3}$ alkyl.

Even more preferred compounds of formula I and II are those, wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl. Further more preferred are compounds of formula I and II, wherein $R^1$ is H or methyl, $R^2$ is methyl or ethyl and $R^3$ is methyl.

The most preferred compounds of the formula I and II are the compounds of formula Ia ($R^1=R^2=R^3=CH_3$), Ib ($R^1=H$; $R^2=R^3=CH_3$), IIa ($R^1=R^2=R^3=CH_3$) and IIb ($R^1=H$; $R^2=R^3=CH_3$), respectively, i.e. compounds of the formula I and II, respectively, wherein $R^1$ is H or methyl, and $R^2$ and $R^3$ are methyl.

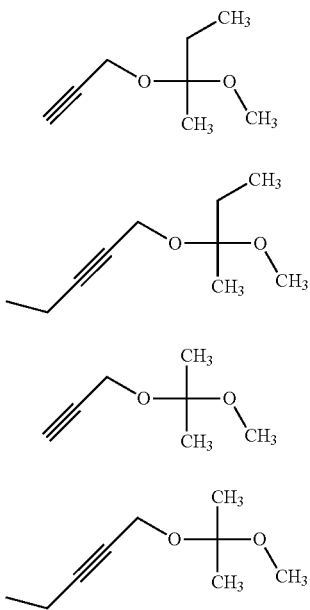

The compounds of formula I and II are novel except of the concrete compound of formula Ib which is not novel. Thus, the present invention is also directed to the novel compounds, i.e. the compounds of the formula I

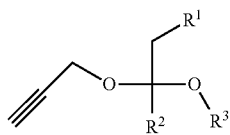

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl; with the proviso that $R^1$ is not H, when $R^2$ and $R^3$ are methyl, as well as to the compounds of formula II

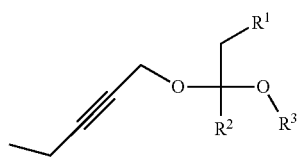

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl.

The process is described in more detail in the following.

Step a)

Catalyst

The acid catalyst used in step a) is preferably selected from the group consisting of Brønsted acids and solid acids.

Preferred examples of Brønsted acids are organic sulphonic acids such as p-TsOH (para-toluene sulphonic acid; preferred among the organic sulphonic acids), $H_2SO_4$ (sulphuric acid) and $H_3PO_4$ (phosphorus acid). $H_3PO_4$ is especially preferred, since then less by-products are formed. Main by-products are the dimers of the formula V:

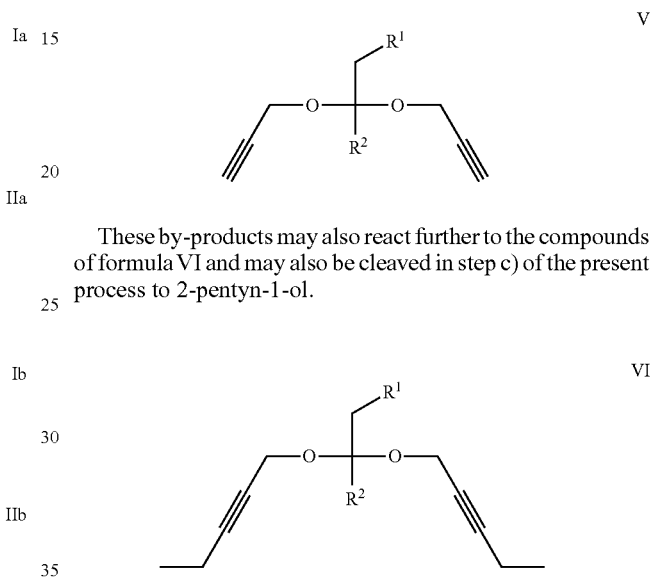

These by-products may also react further to the compounds of formula VI and may also be cleaved in step c) of the present process to 2-pentyn-1-ol.

The Brønsted acids may also be used as solution in organic solvents. $H_3PO_4$ may e.g. be used as 17 weight-% solution in acetone or methanol. $H_2SO_4$ may be used e.g. as aqueous 8 weight-% solution and p-TsOH as monohydrate (p-TsOH.$H_2O$).

Preferred examples of solid acids are Brønsted acids on a carrier, strong acidic cation exchangers and polymers having acidic groups, i.e. functionalized polymers.

Examples of strong acidic cation exchangers are Amberlyst type polymers (e.g. Amberlyst® 15, Amberlyst® 16), Dowex, and polymer bounded p-TsOH (p-toluene sulphonic acid). Especially preferred are Amberlyst® 15 and 16. Amberlyst type polymers, as well as Dowex are all functionalized styrene divinylbenzene copolymers.

The solid acids have preferably a pore diameter in the range of 100 to 500 Å, a surface area of at least 20 m²/g (measured by nitrogen BET), preferably a surface area in the range of 20 to 500 m²/g (more preferably in the range of 25 to 300 m²/g, in the range of 28 to 300 m²/g, in the range of 28 to 70 m²/g, in the range of 30 to 55 m²/g), and a total pore volume of at least 0.10 ml/g, preferably a total pore volume in the range of 0.10 to 0.50 ml/g, more preferably a total pore volume in the range of 0.15 to 0.45 ml/g, even more preferably a total pore volume in the range of 0.18 to 0.42 ml/g, most preferably a total pore volume in the range of 0.20 to 0.40 ml/g; and a concentration of the acid sites (i.e. the sulphonic acid groups) ≥4.0 eq/kg (especially ≥4.5 eq/kg; in the range of 4.5 to 6.0 eq/kg; in the range of 4.5 to 5.5 eq/kg).

Preferably the acidic group of these solid acids is represented by sulphonic acid groups (—$SO_3H$) or by any other group having a $pK_a \leq 4$.

A preferred solid acid is an organic sulphonic acid on a carrier or a polymeric resin with functional sulphonic acid groups.

A further suitable solid acid is a polymer functionalized with $CO_2H$ groups.

Of all the functionalized polymers cited in the context of the present invention the macroreticular polymers are preferred.

Preferably, the immobilized/solid Brønsted acid for use in the present invention has a pka value ≤4, more preferably ≤2.

Examples of immobilized/solid Brønsted acids are organic sulphonic acids, $H_2SO_4$ and $H_3PO_4$, all on a carrier.

The carrier may be either organic or inorganic. Examples of organic carriers are polymers. Examples of inorganic carriers are oxide carriers such as e.g. $SiO_2$, $Al_2O_3$, $TiO_2$, $ZrO_2$ and $GeO_2$.

Examples of Brønsted acids on a carrier are p-toluene sulphonic acid on a polymer or propyl sulphonic acid on silica.

Furthermore, other acid catalysts having a $pK_A$≤4, preferably having a $pK_A$≤2.5, are also suitable for catalyzing the preparation of the ketal of formula I in step a) of the process of the present invention.

Reaction Conditions

Step a) may be carried out in the presence or absence of an organic solvent. If an organic solvent would be present, it would preferably be selected from the group consisting of ethers, ketones, esters and mixtures thereof.

Preferably step a) is carried out in the absence of an organic solvent.

Step a) may be carried out batch-wise or continuously.

Preferably step a) is carried out at a temperature in the range of 0 to 35° C., preferably at a temperature in the range of 3 to 25° C., more preferably at a temperature in the range of 5 to 20° C.

The molar ratio of propargyl alcohol (substrate s) to catalyst (c) is in general in the range of s/c 500 to 500000, preferred in the range of 1000 to 150000, especially preferred in the range of 5000 to 15000.

Step b)

Alkyl Halides

The preferred alkyl halides are ethyl bromide and ethyl iodide, whereby ethyl bromide is the most preferred one.

Lithium Compound

The term "alkyl lithium" encompasses straight $C_{1-6}$-alkyl lithium, as well as branched $C_{3-6}$-alkyl lithium. Preferred examples of alkyl lithium are methyl lithium and n-butyl lithium.

An example for an "aryl lithium" is phenyl lithium.

Lithium amide is the preferred lithium compound. Lithium amide may be prepared according to any process known to the person skilled in the art, e.g. as described by Lambert Brandsma in Chapter 2.3.1.1 of his book "Synthesis of Acetylenes, Allenes and Cumulenes: Methods and Techniques", Elsevier Ltd. UK, 2004, where lithium is added to a mixture of anhydrous liquid ammonia and iron(III) nitrate.

Preferably lithium amide is prepared according to the process as described in EP-A 1 238 944, whose content is incorporated herein by reference. That means that lithium metal is added to ammonia to form "lithium bronze" and this "lithium bronze" is then reacted with a 1,3-diene or an arylolefin in the presence of an organic solvent. In step b) of our process of the present invention the presence of an organic solvent is, however, not necessary. The preparation of lithium amide is preferably carried out in the absence of any organic solvent than ammonia. Preferred olefins for the preparation of lithium amide are 1,3-olefins such as piperylene, isoprene, styrene and myrcene. Piperylene and styrene are especially preferred.

Surprisingly it was found out that such prepared lithium amide leads to a better purity of compound II prepared by it. Thus, the use of such prepared lithium amide is especially advantageous.

Reaction Conditions

Step b) may be carried out in the presence or absence of an organic solvent. Such organic solvent may be selected from the group consisting of ethers, alkanes, olefins, aromatic compounds and mixtures thereof Preferably, however, step b) is carried out in the absence of an organic solvent.

In general step b) is carried out at a temperature and a pressure so that ammonia is liquid under the reaction conditions. At atmospheric pressure the temperature is in the range of −70 to −35° C.

Preferably a lithium amide prepared according to the process of EP-A 1 238 944, especially by the use of piperylene (1,3-pentadiene) or styrene, is used.

Preferably the molar ratio of the lithium compound to the ketal of the formula I is in the range of (1.5-3) to 1, preferably in the range of (1.75-2.5) to 1.

Preferably the molar ratio of the ketal of the formula I to the alkyl halide is in the range of 1:1 to 1:1.5.

Step c)

The acid catalyst used in step c) is preferably selected from the group consisting of Brønsted acids and solid acids. The same Brønsted acids and solid acids as suitable for performing step a) are also suitable for performing step c).

In general acid catalysts having a $pK_A$≤4, preferably a $pK_A$≤2.5, are suitable for the cleavage of the protecting group (step c)).

Preferably Brønsted acids are used for carrying out step c), more preferably the Brønsted acid is selected from the group consisting of p-TsOH, $H_2SO_4$ and $H_3PO_4$.

Most preferably the Brønsted acid used in step c) is $H_2SO_4$.

Step c) is preferably carried out at a temperature in the range of 0 to 50° C., more preferably at a temperature in the range of 5 to 30° C.

The molar ratio of the compound of formula II (substrate s) to the acid catalyst (c) is in general in the range of s/c=(100-2000) to 1, preferably in the range of (200-1000) to 1.

The protic solvent is preferably selected from the group consisting of $H_2O$, alcohols and mixtures thereof.

Preferred examples of alcohols are methanol and ethanol.

If water is used as protic solvent, the molar ratio of water to the ketal of formula II is preferably at least 1:1, more preferably (1.5-3):1.

Advantages of the process according to the present invention are that all steps a) to c) can be carried out without (organic) solvents except ammonia. Furthermore, purification of the intermediates, the compounds of formula II and III, is not necessary. That makes the present process very suitable for large scale production.

Further Embodiments of the Present Invention

A compound of the formula I

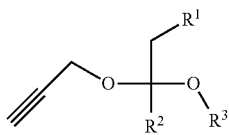

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl; with the proviso that $R^1$ is not H, when $R^2$ and $R^3$ are methyl.

Preferably $R^1=R^2=R^3=$methyl, i.e. a compound of the formula Ia

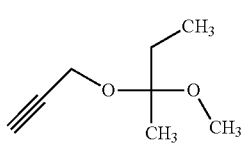

A compound of the formula II

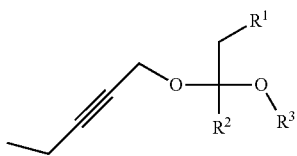

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl.

Preferably $R^1=$H or methyl, $R^2=R^3=$methyl, i.e. compounds of the formula IIa and IIb

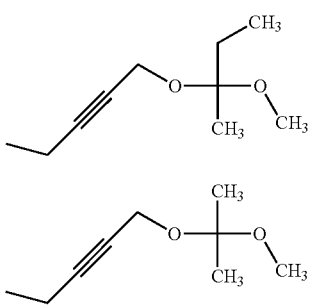

A process for the manufacture of ketals of the formula I,

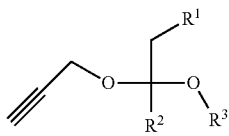

comprising the step of reacting 2-propyn-1-ol with a compound of the formula III in the presence of an acid catalyst

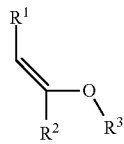

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl.

This process corresponds to step a) of the process described above. All the details given above, including the preferences, also apply here.

A process for the manufacture of ketals of the formula II,

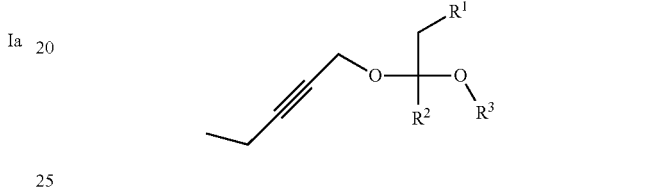

comprising the step of reacting a compound of the formula I with a compound of the formula IV in the presence of ammonia and a lithium compound selected from the group consisting of lithium amide, alkyl lithium and aryl lithium

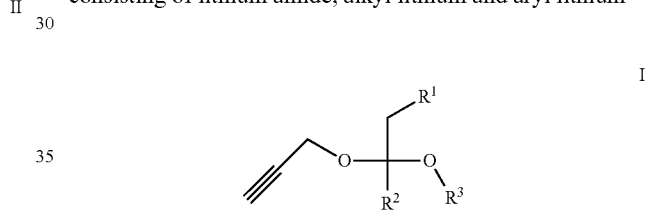

wherein $R^1$ is H or linear $C_{1-6}$ alkyl, $R^2$ is linear $C_{1-6}$ alkyl or branched $C_{3-6}$ alkyl, $R^3$ is linear $C_{1-6}$ alkyl; and X is Cl, Br or I.

This process corresponds to step b) of the process described above. All the details given above, including the preferences, also apply here.

A process for the manufacture of 2-pentyn-1-ol comprising the step of cleaving the hydroxy protecting group from the compound of formula II to obtain 2-pentyn-1-ol by using an acid catalyst in a protic solvent,

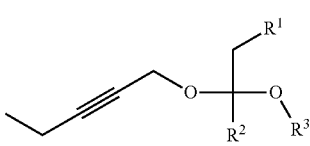

wherein $R^1$ is H or linear $C_{1-6}$ alkyl, $R^2$ is linear $C_{1-6}$ alkyl or branched $C_{3-6}$ alkyl and $R^3$ is linear $C_{1-6}$ alkyl.

This process corresponds to step c) of the process described above. All the details given above, including the preferences, also apply here.

The invention is now further illustrated by the following non-limiting examples.

EXAMPLES

The following abbreviations are used:
BME 2-butenyl methyl ether
GC gas chromatography
IPM Isopropenyl methyl ether
p-TsOH para-toluene sulphonic acid
THP 3,4-dihydro-2H-pyran
General Propargylic alcohol (=2-propyn-1-ol) (Aldrich N° P5.080-3, 99.0% GC), p-toluene sulphonic acid (p-TsOH, Fluka N° 89760, 98.5% GC), Amberlyst 15 (Fluka N° 06423), lithium (Acros, 99.0%), styrene (Fluka 85960, 99.0% GC), bromoethane (=ethyl bromide; Fluka 03150, 98.0%), isoprene (Aldrich 119551, 100.0% GC), myrcene (Givaudan DE-396, 98.0% GC), tetrahydropyrane (THP) (Fluka 37350, 95.0% GC) are commercially available and were used without further purification.

Isopropenyl methyl ether (DSM Nutritional Products Ltd, Lalden (CH), 96.0% GC), butenyl methyl ether (DSM Nutritional Products Ltd, Sisseln (CH), 96.2% GC), and 1,3-pentadiene (=piperylene) (SPC, China, 68.5% GC) were used without further purification.

NMR Spectroscopy

NMR spectra were recorded on a Bruker Avance 300 MHz spectrometer. $^1$H-NMR spectra were recorded at 300 MHz, $^{13}$C spectra were recorded at 75 MHz, respectively. The quantitative spectra were recorded in DMSO-$d_6$ using 1,4 dimethoxybenzene as internal standard. The delay d1 between two pulses was set to 30 s. 12-25 mg samples were used. The spectra have been recorded in CDCl$_3$, δ is given in ppm. The following abbreviations have been used for the multiplicity: S=singlet, d=doublet, t=triplet, q=quadruplet, dd=doublet of doublet, dq=doublet of quadruplet, m=multiplett.

Example 1

Manufacture of 3-(1-methoxy-1-methyl-ethoxy)-propyne

Example 1.1

Use of H$_3$PO$_4$ as Catalyst

25 μl (0.04 mmol) of phosphoric acid (17% w/w in acetone) were added to 22.6 g (399 mmol) of propargylic alcohol at 22° C. The solution was transferred into a dropping funnel 58.8 ml of IPM (600 mmol) were transferred into a second dropping funnel. Both solutions were added simultaneously within 45 minutes to the glass reactor. The internal temperature was maintained between 15° C. and 20° C. during the addition of the reactants. After addition the reaction mixture was held at 15° C. for about 15 minutes. Finally the reaction mixture was concentrated under reduced pressure (40° C., 40 mbar) and the crude product was analyzed by GC. 47.86 g of 3-(1-methoxy-1-methyl-ethoxy)-propyne were obtained with a purity of 96.0%, yield based on propargylic alcohol was 89.85%.

Example 1.2

Use of p-TsOH.H$_2$O as Catalyst 10 mg (0.05 mmol) of p-TsOH monohydrate were dissolved in 22.43 g (396 mmol) of propargylic alcohol at 22° C. The solution was transferred into a dropping funnel. 56.93 ml of IPM (581 mmol) were transferred into a second dropping funnel. Both solutions were added simultaneously within 40 minutes to the glass reactor. The internal temperature was maintained between 15° C. and 20° C. during the addition of the reactant. 100 ml of a saturated sodium bicarbonate solution was added within 5 minutes and the mixture was vigorously stirred for 5 minutes. The solution was extracted with 20 ml n-hexane. Finally the organic phase was concentrated under reduced pressure (40° C., 40 mbar) and the crude product was analyzed by GC. 48.6 g of crude 3-(1-methoxy-1-methyl-ethoxy)-propyne were obtained with a purity of 87.6%, yield based on propargylic alcohol was 83.9%.

Example 1.3

Use of Reduced Amount of p-TsOH.H$_2$O as Catalyst

Example 1.2 was repeated with the same amount of catalyst, but instead of 22.43 g of propargylic alcohol 372 g (6.6 mol) of propargylic alcohol and instead of 56.93 ml of IPM 959 ml (9.8 mol) of IPM were used. Additionally the reaction mixture was stirred for another 15 minutes at 15° C. after the addition of the reactants was completed. With this small amount of catalyst its neutralization with sodium bicarbonate solution as in example 1.2 was not necessary. 852.8 g of crude 3-(1-methoxy-1-methyl-ethoxy)-propyne were obtained with a purity of 89.9%, yield based on propargylic alcohol was 91.0%.

Example 1.4

Use of Amberlyst® 15 as Catalyst

In a jacketed reactor cooled at 10° C. were added 820 mg of Amberlyst 15. A mixture of 372 g (6.6 mol) of propargylic alcohol and 958.5 ml of IPM (9.8 mol) were added within 45 minutes to the reactor. The internal temperature was maintained at 10° C. during the addition of the reactants. After the addition, the reaction mixture was held at 10° C. for about 15 minutes. The catalyst was separated through filtration and the reaction mixture was concentrated under reduced pressure (40° C., 40 mbar). The crude product was analyzed by GC. 881.65 g of crude 3-(1-methoxy-1-methyl-ethoxy)-propyne were obtained with a purity of 90.3%, yield based on propargylic alcohol was 94.6%.

Example 1.5

Use of Amberlyst® 15 as Catalyst—Continuous Mode

Propargylic alcohol (230.4 g, 4.0 mol) and 458.3 g of IPM (6.1 mol) were pumped through a fixed bed reactor (length: 10 cm, diameter: 9 mm) filled with 100 mg of Amberlyst®15 (feed rate of propargylic alcohol=1 ml/min., feed rate of IPM=2.5 ml/min) at 10° C. for 4 hours. During 1 hour a solution of 343.1 g was collected. The excess of IPM was distilled under reduced pressure (40° C., 40 mbar) and the crude product was analyzed by GC. Crude 3-(1-methoxy-1-methyl-ethoxy)-propyne (243.2 g) was obtained with a purity of 95.9% (91.0% yield based on propargylic alcohol).

Example 1.6

Use of H$_2$SO$_4$ as Catalyst

5 μl (4 μmol) of sulfuric acid (8% w/w) were added to 22.6 g (399 mmol) of propargylic alcohol at 22° C. The solution was transferred into a dropping funnel 58.75 ml of IPM (599 mmol) were transferred into a second dropping funnel Both solutions were added simultaneously within 45 minutes to the glass reactor. The internal temperature was maintained between 15° C. and 20° C. during the addition of the reactants. After addition the reaction mixture was held at 15° C. for about 15 minutes. Finally the reaction mixture was concentrated under reduced pressure (40° C., 40 mbar) and the crude product was analyzed by GC. 51.0 g of 3-(1-methoxy-1-methyl-ethoxy)-propyne were obtained with a purity of 87.4%, yield based on propargylic alcohol was 87.2%.

Example 2

Manufacture of 2-methoxy-2-prop-2-ynyloxy-butane

Example 2.1

Use of $H_3PO_4$ as Catalyst

A mixture of 130 mg (0.3 μmol) of phosphoric acid (19% w/w in acetone) and 22.80 g (399 mmol) of propargyl alcohol is filled into a dropping funnel. 53.5 g (598 mmol) of 2-methoxy-but-2-ene (96.2% GC) was transferred into a second dropping funnel. Both solutions were added simultaneously within 30 minutes to the cooled flask (8° C.). The internal temperature was maintained between 8° C. and 12° C. during the addition of the reactants. The reaction mixture was held at 10° C. for about 2 hours. The reaction mixture was neutralized with 0.5 g of sodium carbonate and concentrated under reduced pressure (40° C., 80 mbar). The crude product was analyzed by GC. 58.0 g of crude 2-methoxy-2-prop-2-ynyloxy-butane were obtained with a purity of 85.5% (yield 96.9% based on propargyl alcohol).

Example 3

Manufacture of 1-(1-methoxy-1-methyl-ethoxy)-pent-2-yne

Example 3.1

Use of Lithium Amide—Prepared with Styrene—as Base 883 mg (126 mmol) of granulated lithium were added within 5 minutes to 107 g (6.30 mol) of liquid ammonia at −38° C. The mixture was stirred until no more lithium floated (after approximately 10 minutes). A dark blue solution of lithium in liquid ammonia was obtained. 14.6 g (140 mmol) of styrene were added portion wise within 20 minutes. The end of the formation of lithium amide could be recognized by the discoloration of the reaction mixture. 9.9 g (70 mmol) of 3-(1-methoxy-1-methyl-ethoxy)-propyne (90.8% GC) were added with a dropping funnel to the reaction mixture at −38° C. within 20 minutes. The reaction mixture was held at −38° C. for about 1 hour. 14 g (126 mmol) of bromoethane were added with a dropping funnel to the reaction mixture within 20 minutes. The reaction mixture was subsequently stirred for 1 hour. 100 ml of n-hexane were added to the reaction mixture and the liquid ammonia was evaporated under normal pressure within 16 hours. 70 ml of water were added to the reaction mixture at 22° C., and the mixture was stirred until all salt was dissolved. The organic layer was separated and dried over 2 g of anhydrous magnesium sulfate. The solution was concentrated under reduced pressure (40° C., 40 mbar) and the crude product was analyzed by GC. 10.6 g of 1-(1-methoxy-1-methyl-ethoxy)-pent-2-yne were obtained with a purity of 84.4% (yield 81.8%, based on 3-(1-methoxy-1-methyl-ethoxy)-propyne).

Example 3.2

Use of Lithium Amide—Prepared with Isoprene—as Base 259 mg (37 mmol) of granulated lithium were added within 5 minutes to 47.7 g (1.9 mol) of liquid ammonia at −40° C. The mixture was stirred until no more lithium floated (after approximately 10 minutes). A dark blue solution of lithium in liquid ammonia was obtained. 4.0 ml (40 mmol) of isoprene were added portion wise within 10 minutes. The end of the formation of lithium amide could be recognized by the discoloration of the reaction mixture. 2.9 g (20 mmol) of 3-(1-methoxy-1-methyl-ethoxy)-propyne (88.9% GC) were added with a dropping funnel to the reaction mixture at −40° C. within 20 minutes. The reaction mixture was held at −40° C. for about 1 hour. 8.9 g (80 mmol) of bromoethane were added with a dropping funnel to the reaction mixture within 10 minutes. The reaction mixture was subsequently stirred for 1 hour. 20 ml of n-hexane were added to the reaction mixture and the liquid ammonia was evaporated under normal pressure within 5 hours. 20 ml of water were added to the reaction mixture at 22° C., and the mixture was stirred until all salt was dissolved. The organic layer was separated and dried over 2 g of anhydrous magnesium sulfate. The solution was concentrated under reduced pressure (40° C., 40 mbar) and the crude product was analyzed by GC. 3.3 g of crude 1-(1-methoxy-1-methyl-ethoxy)-pent-2-yne were obtained with a purity of 75.6% (yield 80.0% based on 3-(1-methoxy-1-methyl-ethoxy)-propyne).

Example 3.3

Use of Lithium Amide—Prepared with Myrcene—as Base 0.89 g (127 mmol) of granulated lithium were added within 15 minutes to 200 ml (8 mol) of liquid ammonia at −37° C. The mixture was stirred until no more lithium floated (after approximately 15 minutes). A dark blue solution of lithium in liquid ammonia was obtained. 12.6 g (91 mmol) of myrcene were added portion wise within 30 minutes. The end of the formation of lithium amide could be recognized by the discoloration of the reaction mixture. 10.0 g (71 mmol) of 3-(1-methoxy-1-methyl-ethoxy)-propyne (90.8% GC) were added with a dropping funnel to the reaction mixture at −37° C. within 30 minutes. The reaction mixture was held at −37° C. for about 1 hour. 14.0 g (126 mmol) of bromoethane were added with a dropping funnel to the reaction mixture within 30 minutes. The reaction mixture was subsequently stirred for 1 hour. 157 ml of n-hexane were added to the reaction mixture and the liquid ammonia was evaporated under normal pressure within 15 hours. 50 ml of water were added to the reaction mixture at 22° C., and the mixture was stirred until all salt was dissolved. The organic layer was separated and concentrated under reduced pressure (40° C., 40 mbar). The crude product was analyzed by GC. 25.8 g of crude 1-(1-methoxy-1-methyl-ethoxy)-pent-2-yne were obtained (yield 83.0% based on 3-(1-methoxy-1-methyl-ethoxy)-propyne).

Example 3.4

Use of Lithium Amide—Prepared with 1,3-pentadiene—as Base 0.89 g (127 mmol) of granulated lithium were added within 20 minutes to 100 ml (4 mol) of liquid ammonia at −37° C.

The mixture was stirred until no more lithium floated (after approximately 15 minutes). A dark cyan solution of lithium in liquid ammonia was obtained. 6.34 g (92 mmol) of piperylene (=1,3-pentadiene) were added portion wise within 30 minutes. The end of the formation of lithium amide could be recognized by the discoloration of the reaction mixture. 10.1 g (71 mmol) of 3-(1-methoxy-1-methyl-ethoxy)-propyne (89.7% GC) were added with a dropping funnel to the reaction mixture at −37° C. within 30 minutes. The reaction mixture was held at −37° C. for about 1 hour. 14.0 g (126 mmol) of bromoethane were added with a dropping funnel to the reaction mixture within 30 minutes. The reaction mixture was subsequently stirred for 1 hour. 100 ml of n-hexane were added to the reaction mixture and the liquid ammonia was evaporated under normal pressure within 1.5 hours. 50 ml of water were added to the reaction mixture at 22° C., and the mixture was vigorously stirred until all salt was dissolved. The water layer was extracted once with 50 ml of n-hexane. The organic layer was dried over 5 g of anhydrous sodium sulfate. The solution was concentrated under reduced pressure (40° C., 60 mbar) and the crude product was analyzed by GC. 11.3 g of crude 1-(1-methoxy-1-methyl-ethoxy)-pent-2-yne were obtained with a purity of 87.5% (yield 85.3% based on 3-(1-methoxy-1-methyl-ethoxy)-propyne).

Example 3.5

Use of Ethyl Iodide Instead of Ethyl Bromide 0.89 g (127 mmol) of granulated lithium were added within 15 minutes to 100 ml (4 mol) of liquid ammonia at −37° C. The mixture was stirred until no more lithium floated (after approximately 15 minutes). A dark blue solution of lithium in liquid ammonia was obtained. 5.94 g (86.3 mmol) of isoprene were added portion wise within 30 minutes. The end of the formation of LiNH$_2$ could be recognized by the de-coloration of the reaction mixture and 10.69 g (70.1 mmol) of 3-(1-methoxy-1-methyl-ethoxy)-propyne were added to the reaction mixture at −37° C. within 30 minutes. The reaction mixture was held at −37° C. for about 1 hour. Ethyl iodide (20.05 g, 126 mmol) was added with a dropping funnel to the reaction mixture within 30 minutes. The reaction mixture was subsequently stirred for 1 hour. n-Hexane (100 ml) was added to the reaction mixture and the liquid ammonia was evaporated under normal pressure within 1.5 hours. Water (50 ml) was added to the reaction mixture at 22° C., and the mixture was vigorously stirred until all salt was dissolved. The water layer was extracted twice with 50 ml n-hexane. The organic layer was dried over 5 g of anhydrous sodium sulfate. The solution was concentrated under reduced pressure (40° C., 60 mbar) and the crude product was analyzed by GC. Crude 1-(1-methoxy-1-methyl-ethoxy)-pent-2-yne (13.21 g) were obtained with a purity of 72.95% (88.0% yield based on 3-(1-methoxy-1-methyl-ethoxy)-propyne).

Example 4

Manufacture of 1-(1-methoxy-1-methyl-propoxy)-pent-2-yne

Example 4.1

Use of Lithium Amide—Prepared with Isoprene—as Base 890 mg (127 mmol) of granulated lithium were added within 5 minutes to 100 ml (4.0 mol) of liquid ammonia at −40° C. The mixture was stirred until no more lithium floated (after approximately 10 minutes). A dark blue solution of lithium in liquid ammonia was obtained. 5.94 g (86.6 mmol) of isoprene was added portion wise within 10 minutes, whereas the solution gets white at the end of the addition. The mixture was stirred for 25 minutes at −38° C. 9.1 g (69.5 mmol) of 2-methoxy-2-prop-2-ynyloxy-butane (97.4% GC) were added with a dropping funnel to the reaction mixture at −38° C. within 25 minutes. The reaction mixture was held at −38° C. for about 1 hour. 14 g (128.5 mmol) of bromoethane were added with a dropping funnel to the reaction mixture within 20 minutes. The reaction mixture was subsequently stirred for 1 hour. 100 ml of n-hexane were added to the reaction mixture and the liquid ammonia was evaporated under normal pressure within 1 hour and 30 minutes. 50 ml of water was added to the reaction mixture at 40° C., and the mixture was stirred until all salt was dissolved. The mixture is transferred into a separatory funnel and the layers were separated. The aqueous layer is extracted with 127 ml of n-hexane. The organic layers were dried over 0.5 g of anhydrous sodium sulphate and concentrated under reduced pressure (40° C., 60 mbar), and the crude product (1-(1-methoxy-1-methyl-propoxy)-pent-2-yne) was analyzed by GC. 10.54 g of crude 1-(1-methoxy-1-methyl-propoxy)-pent-2-yne were obtained with a purity of 87.1% (yield 77.6% based on 2-methoxy-2-prop-2-ynyloxy-butane).

Example 5

Manufacture of 2-pentyn-1-ol Starting from 1-(1-methoxy-1-methyl-ethoxy)-pent-2-yne Example 5.1

Use of p-toluenesulfonic acid as Catalyst 5.0 g (25.7/24.387 mmol) of 1-(1-methoxy-1-methyl-ethoxy)-pent-2-yne (purity: 80.4% according to GC) were diluted at 20° C. in 100 ml of n-hexane (technical grade). 20 mg of para-toluenesulfonic acid monohydrate and 500 μl (27.8 mmol) of de-ionized water were added under stirring at 22° C. to the solution. The mixture was held at 22° C. for about 1 hour and 45 minutes. 500 mg (4.7 mmol) of sodium carbonate were added and the reaction mixture was subsequently stirred for 5 minutes. The salt waste was separated through filtration. Finally the solution was concentrated under reduced pressure (40° C., 50 mbar) and the crude product was analyzed by GC. 2.23 g of crude 2-pentyn-1-ol (purity: 78.62% according to GC) were obtained (yield 85.5% based on 1-(1-methoxy-1-methyl-ethoxy)-pent-2-yne).

Example 5.2

Use of aqueous 8 Weight-% H$_2$SO$_4$ Solution as Catalyst 5.0 g (25.7 mmol) of 3 (80.4% GC) was diluted at 20° C. in 100 ml of n-hexane. 93 μl (0.1 mmol) of sulfuric acid (8% w/w) and 440 μl (24.4 mmol) of water were added under stirring at 22° C. to the solution. The mixture was held at 22° C. for about 1 hour and 30 minutes. The solution was neutralized with 500 mg (4.7 mmol) of sodium carbonate and the salt waste was separated through filtration. Finally the solution was concentrated under reduced pressure (40° C., 50 mbar) and the crude product was analyzed by GC. 2.26 g of crude 2-pentyn-1-ol were obtained with a purity of 81.2% (yield 85.3% based on 1-(1-methoxy-1-methyl-ethoxy)-pent-2-yne).

Example 5.3

Use of Amberlyst 15 as Catalyst 25 mg of Amberlyst® 15 [Amberlyst 15 WET] were added under an Argon atmosphere at 22° C. to a mixture of 7.5 g (45.6 mmol) of 1-(1-methoxy-1-methyl-ethoxy)-pent-2-yne (purity: 95% according to GC) and 3.75 ml (208 mmol) of de-ionized water. The mixture was held under stirring at 22° C. for about 1 hour and 30 minutes. The catalyst was separated through filtration. 2-pentyn-1-ol was extracted with a total amount of 60 ml of diethyl ether and the organic layer was dried over 5 g of sodium sulfate anhydrous. The solution was concentrated under reduced pressure (40° C., 50 mbar) and the crude product was analyzed by GC. 3.85 g of crude 2-pentyn-1-ol were obtained with a purity of 95.0% (yield 95.3% based on 1-(1-methoxy-1-methyl-ethoxy)-pent-2-yne).

Example 5.4

Use of Aqueous 8 Weight-% $H_2SO_4$ Solution as Catalyst and the Dimer 1-(1-methyl-1-pent-2-yny-loxy-ethoxy)-pent-2-yne as Further Starting Material 213 μl (0.2 mmol) of aqueous 8 weight-% sulfuric acid and 1169 μl (65 mmol) of water were added under stirring at 22° C. to 12.7 g (total 61.1 mmol of 1-(1-methoxy-1-methyl-ethoxy)-pent-2-yne) of a mixture of 1-(1-methoxy-1-methyl-ethoxy)-pent-2-yne (72.5% GC) and 1-(1-methyl-1-pent-2-ynyloxy-ethoxy)-pent-2-yne (3.5% GC). The emulsion was held at 22° C. for about 1 hour and 30 minutes. The resulting reaction mixture was purified by bulb-to-bulb distillation (P=65 mbar/oven temperature 97-100° C.) and the end product was analyzed by GC. Two fractions of 2-pentyn-1-ol were distilled with a purity of 99.7% and 89.4% (yield after distillation was 94.5% based on 1-(1-methoxy-1-methyl-ethoxy)-pent-2-yne+1-(1-methyl-1-pent-2-ynyloxy-ethoxy)-pent-2-yne).

Example 5.5

Use of Aqueous 8 Weight-% $H_2SO_4$ Solution as Catalyst

180 μl (0.16 mmol) of aqueous 8 weight-% sulfuric acid and 900 μl (50 mmol) of water were added under stirring at 22° C. to 10.8 g (59 mmol) of 1-(1-methoxy-1-methyl-ethoxy)-pent-2-yne. The emulsion was held at 22° C. for about 1 hour and 30 minutes. The resulting reaction mixture was purified by bulb-to-bulb distillation (P=65 mbar/oven temperature 97-100° C.) and the final product was analyzed by GC. Two fractions of 2-pentyn-1-ol were distilled with a purity of 97.3% and 89.5% (yield after distillation was 89.8% based on 1-(1-methoxy-1-methyl-ethoxy)-pent-2-yne).

Example 6

Manufacture of 2-pentyn-1-ol Starting from 1-(1-methoxy-1-methyl-propoxy)-pent-2-yne

Example 6.1

Use of Aqueous 8 Weight-% $H_2SO_4$ Solution as Catalyst

A 3-necked flask is filled with 2.89 (16.7 mmol) of 1-(1-methoxy-1-methyl-propoxy)-pent-2-yne (98.6% GC), 60 μl (0.05 mmol) of sulfuric acid (8% w/w) and 285 μl (15.8 mmol) of water. The solution was stirred at 22° C. for about 1 hour and 30 minutes. The solution was neutralized with 500 mg (4.7 mmol) of sodium carbonate and then dried over 500 mg of sodium sulfate anhydrous. After filtration of the salt waste, the mixture was concentrated under reduced pressure (40° C., 50 mbar) and the crude product was analyzed by GC. 1.35 g of crude 2-pentyn-1-ol were obtained with a purity of 92.8% (yield 89.0% based on 1-(1-methoxy-1-methyl-propoxy)-pent-2-yne).

Example 6.2

Use of Aqueous 8 Weight-% $H_2SO_4$ Solution as Catalyst

A 3-necked flask is filled with 2.89 (16.7 mmol) of 1-(1-methoxy-1-methyl-propoxy)-pent-2-yne, 60 μl (0.05 mmol) of aqueous 8 weight-% sulfuric acid and 285 μl (15.8 mmol) of water. The solution was stirred at 22° C. for about 1 hour and 30 minutes. The solution was neutralized with 500 mg (4.7 mmol) of sodium carbonate and then dried over 500 mg of sodium sulfate anhydrous. After filtration of the salt waste, the mixture was concentrated under reduced pressure (40° C., 50 mbar) and the crude product was analyzed by GC. Crude 2-pentyn-1-ol (1.35 g) was obtained in purity of 92.8% (89.0% yield based on 1-(1-methoxy-1-methyl-propoxy)-pent-2-yne).

COMPARATIVE EXAMPLES

Comparative Example A

Synthesis of 2-pentyn-1-ol Using THP as Protective Group

A.1 Preparation of 2-prop-2-ynyloxy-tetrahydropyran by use of Amberlyst 15 as Catalyst A jacketed reactor cooled at 10° C. was filled with 150 mg of Amberlyst 15. A mixture of 7.53 g (133 mmol) propargylic alcohol and 17.66 g of THP (199 mmol) was added within 45 minutes. The internal temperature was maintained at 10° C. during the addition of the reactants. The reaction mixture was held at 10° C. for about 15 minutes. The catalyst was separated through filtration and the reaction mixture was concentrated under reduced pressure (40° C., 40 mbar) and the crude product was analyzed by GC. Crude 2-prop-2-ynyloxy-tetrahydropyran (20.89 g) was obtained with a purity of 87.1% (97.6% yield based on propargylic alcohol).

A.2 Preparation of 2-pent-2-ynyloxy-tetrahydro-pyran in Liquid Ammonia, Lithium Amide Prepared with Isoprene 0.89 g (127 mmol) of granulated lithium were added within 5 minutes to 100 ml (4 mol) of liquid ammonia at −38° C. The mixture was stirred until no more lithium floated (after approximately 10 minutes). A dark blue solution of lithium in liquid ammonia was obtained. Isoprene (5.94 g, 86 mmol) was added portion wise within 20 minutes. The reaction mixture was held at −38° C. for about 15 minutes. The end of the formation of Li-amide could be recognized by the de-coloration of the reaction mixture. 11.33 g (70 mmol) of 2-prop-2-ynyloxy-tetrahydropyran were added via a dropping funnel to the reaction mixture at −38° C. within 20 minutes. The reaction mixture was held at −38° C. for about 1 hour. Ethyl bromide 14.0 g (126 mmol) was added via a dropping funnel to the reaction mixture within 20 minutes. The reaction mixture was subsequently stirred for 1 hour. 100 ml n-hexane was added to the reaction mixture and the liquid ammonia was evaporated under normal pressure within 1.5 hours. 50 ml of water was added to the reaction mixture at 22° C., and the mixture was stirred until all salt was dissolved. The water layer was extracted twice with 50 ml n-hexane. The organic layer was dried over 5 g of anhydrous sodium sulfate. The solution was concentrated under reduced pressure (40° C., 60 mbar) and the crude product was analyzed by GC. Crude 2-pent-2-ynyloxy-tetrahydro-pyran (12.4 g) was obtained with a purity of 90.1% (94.3% yield based on 2-prop-2-ynyloxy-tetrahydropyran).

A.3 Preparation of 2-pentyn-1-ol from 2-pent-2-ynyloxy-tetrahydro-pyran Catalyzed with Aqueous 8 Weight-% $H_2SO_4$ 200 µl (0.2 mmol) of aqueous 8 weight-% of sulfuric acid, 200 µl (11 mmol) of water and 20 ml (789 mmol) of methanol were added under stirring at 22° C. to 1.0 g (5.4 mmol) of 2-pent-2-ynyloxy-tetrahydro-pyran. The reaction mixture was held at reflux (temperature: 65° C.) for about 2 hours. The reaction mixture was neutralized with 0.5 g of sodium carbonate. The methanol was evaporated under reduced pressure (40° C., 60 mbar). The residue was diluted in 100 ml ethyl acetate and the mixture was dried over sodium sulfate anhydrous. After filtration of salt waste the solution was evaporated under reduced pressure (40° C., 60 mbar) and the crude product was analyzed by GC. Crude 2-pentyn-1-ol (0.5 g) was obtained with a purity of 82.2% (91.3% yield based on 2-pent-2-ynyloxy-tetrahydro-pyran).

Analytical Data

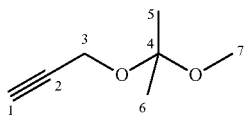

IR (ATR, cm$^{-1}$): 3293 (w, —CCH), 2993, 2944 (m, —CH$_3$, —CH$_2$—CH$_3$, —CH$_2$—), 2832 (w, —OCH$_3$), 2121 (w, —CCH), 1461 (m, —CH$_2$—), 1379 (s).

$^1$H-NMR (300 MHz, CDCl$_3$): δ=4.11 (d, J=2.5 Hz, 2H, H3), 3.23 (s, 3H, H7), 2.39 (t, J=2.5 Hz, 1H, H1), 1.38 (s, 6H, H5, H6).

$^{13}$C-NMR (75 MHz, CDCl$_3$): δ=100.9 (C4), 80.9 (C2), 73.1 (C1, $^1J_{C,H}$=243 Hz), 49.0 (C3), 48.8 (C7), 24.3 (C5, C6).

MS (EI) m/z (rel. intensity, %): 113 [M$^+$-CH$_3$, 15], 97 [M$^+$-OCH$_3$, 27], 73 [M$^+$-C(CH$_3$)$_2$(OCH$_3$), 55].

Microanalysis: calc. for C$_7$H$_{12}$O$_2$ (MW 128.17), C, 65.60; H, 9.44; O, 24.97. found: C, 64.82; H, 9.08; O, 25.81.

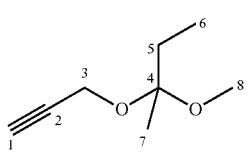

IR (ATR, cm$^{-1}$): 3294 (w, —CCH), 2975, 2945 (m, —CH$_3$, —CH$_2$—CH$_3$, —CH$_2$—), 2832 (w, —OCH$_3$), 2121 (w, —CCH), 1463 (m, —CH$_2$—), 1381 (s).

$^1$H-NMR (300 MHz, CDCl$_3$): δ=4.10-3.96 (m, 2H, H3), 3.14 (s, 3H, H8), 2.31 (t, J=2.5 Hz, 1H, H1), 1.63-1.55 (q, J=7.4 Hz, 2H, H5), 1.22 (s, 3H, H7), 0.84 (t, J=7.5 Hz, 3H, H6).

$^{13}$C-NMR (75 MHz, CDCl$_3$): δ=103.1 (C4), 80.9 (C2), 73.0 (C1, $^1J_{C,H}$=258 Hz), 48.6 (C3), 48.5 (C8), 29.4 (C5), 20.7 (C7), 8.5 (C6).

MS (EI) m/z (rel. intensity, %): 127 [M$^+$-CH$_3$, 9], 87 [M$^+$-C(CH$_3$)(CH$_2$CH$_3$)(OCH$_3$), 91].

Microanalysis: calc. for C$_8$H$_{14}$O$_2$ (MW 142.20), C, 67.57; H, 9.92; O, 22.50. found: C, 66.65; H, 9.97; O, 22.90.

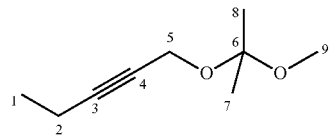

IR (ATR, cm$^-$): 2990, 2940, 2880 (m, —CH$_3$, —CH$_2$—CH$_3$, —CH$_2$—), 2830 (w, —OCH$_3$), 2210 (w, —CCH), 1459 (m, —CH$_2$—), 1379 (s).

$^1$H-NMR (300 MHz, CDCl$_3$): δ=4.09 (t, J=2.1 Hz, 2H, H5), 3.23 (s, 3H, H9), 2.27-2.19 (m, 2H, H2), 1.37 (s, 6H, H7, H8), 1.14 (t, J=7.4 Hz, 3H, H1).

$^{13}$C-NMR (75 MHz, CDCl$_3$): δ=100.6 (C6), 87.0 (C3), 76.1 (C4), 49.5 (C5), 48.7 (C9), 24.4 (C7, C8), 13.7 (C1), 12.6 (C2).

MS (EI) m/z (rel. intensity, %): 141 [M$^+$-CH$_3$, 9], 125 [M$^+$-OCH$_3$, 7], 73 [M$^+$-C(CH$_3$)$_2$(OCH$_3$), 65], 67 [M$^+$-CH$_2$CCCH$_2$CH$_3$, 19].

Microanalysis: calc. for C$_9$H$_{16}$O$_2$ (MW 156.23), C, 69.19; H, 10.32; O, 20.48. found: C, 68.53; H, 10.20; O, 21.18.

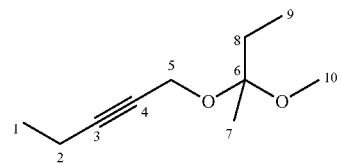

IR (ATR, cm$^-$): 2976, 2941, 2883, 2832 (s, —CH$_3$, —CH$_2$—CH$_3$, —CH$_2$—), 2832 (w, —OCH$_3$), 2210 (w, —CCH), 1461 (m, —CH$_2$—), 1379 (s).

$^1$H NMR (300 MHz, CDCl$_3$): δ=4.01-3.99 (q, J=1.1, 2.1 Hz, 2H, H5), 3.14 (s, 3H, H10), 2.20-2.11 (m, 2H, H2), 1.63-1.55 (q, J=7.5 Hz, 2H, H8), 1.22 (s, 3H, H7), 1.09-1.04 (t, J=7.5 Hz, 3H, H1), 0.86-0.81 (t, J=7.5 Hz, 3H, H9).

$^{13}$C NMR (75 MHz, CDCl$_3$): δ=101.9 (C3), 85.9 (C6), 75.1 (C4), 48.2 (C10), 47.4 (C5), 28.4 (C8), 19.8 (C7), 12.8 (C1), 11.6 (C2), 7.5 (C9).

MS (EI) m/z (rel. intensity, %): 155 [M$^+$-CH$_3$, 1], 141 [M$^+$-CH$_2$CH$_3$, 11], 87 [M$^+$-C(CH$_3$)(CH$_2$CH$_3$)(OCH$_3$), 55], 67 [M$^+$-CH$_2$CCCH$_2$CH$_3$, 34].

Microanalysis: calc. for C$_{10}$H$_{18}$O$_2$ (MW 170.25), C, 70.55; H, 10.66; O, 18.79. found: C, 69.54; H, 10.55; O, 20.19.

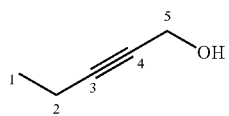

IR (ATR, cm$^{-1}$): 3327 ($s_{br}$, OH), 2977, 2938, 2878 (s, —CH$_3$, —CH$_2$—CH$_3$, —CH$_2$—), 2230 (w, —CCH), 1455 (s, —CH$_2$—), 1319 (s).

$^1$H-NMR (300 MHz, CDCl$_3$): δ=4.25 (t, J=2.1 Hz, 2H, H5), 2.28-2.18 (m, 2H, H2), 2.02 ($s_{br}$, 1H, OH), 1.15 (t, J=7.5 Hz, 3H, H1).

$^{13}$C-NMR (75 MHz, CDCl$_3$): δ=87.8 (C3), 77.7 (C4), 51.3 (C5), 13.8 (C1), 12.4 (C2).

MS (EI) m/z (rel. intensity, %): 83 [M$^+$-H, 27], 65 [M$^+$-H$_2$O, 9], 55 [M$^+$-CH$_2$CH$_3$, 36], 39 [M$^+$-CH$_2$CH$_3$, —OH, 28].

Microanalysis: calc. for C$_5$H$_8$O (MW 84.12), C, 71.39; H, 9.59; O, 19.02. found: C, 70.20; H, 9.46; O, 20.10.

The invention claimed is:

1. A process for the manufacture of 2-pentyn-1-ol starting from 2-propyn-1-ol comprising the following steps:
   a) preparing a ketal of the formula I starting from 2-propynol in the presence of an acid catalyst;

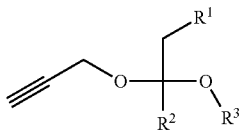

b) reacting the ketal of formula I with an alkyl halide selected from the group consisting of ethyl chloride, ethyl bromide and ethyl iodide to the ketal of formula II in the presence of ammonia and a lithium compound selected from the group consisting of lithium amide, alkyl lithium and aryl lithium;

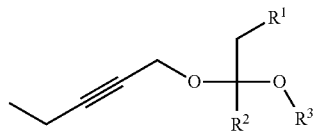

c) reacting the ketal of the formula II to 2-pentyn-1-ol in the presence of an acid catalyst and a protic solvent;
   wherein R$^1$ is H or linear C$_{1-6}$ alkyl, R$^2$ is linear C$_{1-6}$ alkyl or branched C$_{3-6}$ alkyl and R$^3$ is linear C$_{1-6}$ alkyl.

2. The process according to claim 1, wherein the acid catalyst used in at least one of steps a) and c) is selected from the group consisting of Brønsted acids and solid acids.

3. The process according to claim 2, wherein the acid catalyst has a pK$_A$≤4.

4. The process according to claim 2, wherein the Brønsted acid is selected from the group consisting of p-TsOH, H$_2$SO$_4$ and H$_3$PO$_4$.

5. The process according to claim 2, wherein the solid acid is selected from the group consisting of Brønsted acids on a carrier, strong acidic cation exchangers and polymers having acidic groups.

6. The process according to claim 1, wherein at least one of steps a) and b) is carried out in the absence of an organic solvent.

7. The process according to claim 1, wherein step a) is carried out at a temperature in the range of 0 to 35° C.

8. The process according to claim 1, wherein step b) is carried out at a temperature and a pressure so that ammonia is liquid under the reaction conditions.

9. The process according to claim 1, wherein step c) is carried out at a temperature in the range of 0 to 50° C.

10. The process according to claim 1, wherein R$_1$ is H or methyl, and R$_2$ and R$_3$ are methyl.

11. A compound of the formula I

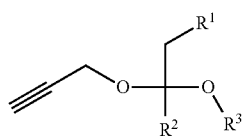

wherein R$_1$ is H or linear C$_{1-6}$ alkyl, R$_2$ is linear C$_{1-6}$ alkyl or branched C$_{3-6}$ alkyl and R$_3$ is linear C$_{1-6}$ alkyl; with the proviso that R$_1$ is not H, when R$_2$ and R$_3$ are methyl.

12. The compound of the formula I according to claim 11, wherein R$_1$=R$_2$=R$_3$=methyl.

13. A compound of the formula II

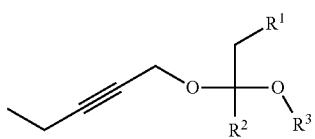

wherein R$_1$ is H or linear C$_{1-6}$ alkyl, R$_2$ is linear C$_{1-6}$ alkyl or branched C$_{3-6}$ alkyl and R$_3$ is linear C$_{1-6}$ alkyl.

14. The compound of the formula II according to claim 13, wherein R$_1$=H or methyl and R$_2$=R$_3$=methyl.

15. A process for the manufacture of ketals of the formula I,

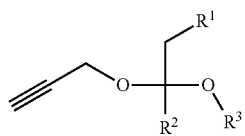

comprising the step of reacting 2-propyn-1-ol with a compound of the formula III in the absence of an organic solvent and in the presence of an acid catalyst:

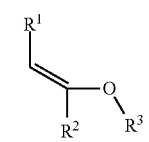

wherein R$_1$ is H or linear C$_{1-6}$ alkyl, R$_2$ is linear C$_{1-6}$ alkyl or branched C$_{3-6}$ alkyl and R$_3$ is linear C$_{1-6}$ alkyl.

16. A process for the manufacture of ketals of the formula II,

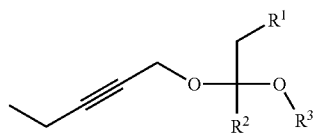

comprising the step of reacting a compound of the formula I with a compound of the formula IV in the presence of ammonia and a lithium compound selected from the group consisting of lithium amide, alkyl lithium and aryl lithium,

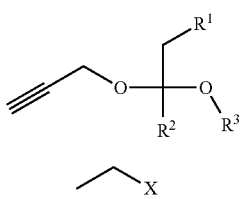

wherein $R_1$ is H or linear $C_{1-6}$ alkyl, $R_2$ is linear $C_{1-6}$ alkyl or branched $C_{3-6}$ alkyl, $R_3$ is linear $C_{1-6}$ alkyl; and X is Cl, Br or I.

17. The process according to claim 16, wherein X is Br.

18. A process for the manufacture of 2-pentyn-1-ol comprising the step of cleaving the hydroxy protecting group from the compound of formula II to obtain 2-pentyn-1-ol by using an acid catalyst in a protic solvent,

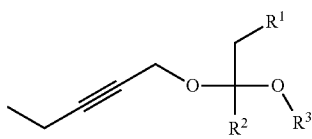

wherein $R_1$ is H or linear $C_{1-6}$ alkyl, $R_2$ is linear $C_{1-6}$ alkyl or branched $C_{3-6}$ alkyl and $R_3$ is linear $C_{1-6}$ alkyl.

19. The process according to claim 15, wherein $R_1$ is H or methyl, and $R_2$ and $R_3$ are methyl.

* * * * *